United States Patent
Edie et al.

(10) Patent No.: US 8,372,148 B2
(45) Date of Patent: Feb. 12, 2013

(54) EXPANDABLE INTERVERTEBRAL SPACERS AND METHODS OF USE

(75) Inventors: Jason A. Edie, Salt Lake City, UT (US); Lloyd Guyton Bowers Cooper, Birmingham, AL (US); Don Byron Walker, II, Muscle Shoals, AL (US)

(73) Assignee: Warsaw Orthpedic, Inc., Warsaw, IN (US)

( * ) Notice: Subject to any disclaimer, the term of this patent is extended or adjusted under 35 U.S.C. 154(b) by 0 days.

(21) Appl. No.: 13/156,769

(22) Filed: Jun. 9, 2011

(65) Prior Publication Data
US 2011/0238182 A1    Sep. 29, 2011

Related U.S. Application Data

(63) Continuation of application No. 12/848,499, filed on Aug. 2, 2010, now Pat. No. 7,998,210, which is a continuation of application No. 11/412,671, filed on Apr. 27, 2006, now Pat. No. 7,794,501.

(51) Int. Cl.
   *A61F 2/44* (2006.01)
(52) U.S. Cl. .................................................. 623/17.12
(58) Field of Classification Search ............... 623/17.12, 623/17.11–17.16
   See application file for complete search history.

(56) References Cited

U.S. PATENT DOCUMENTS

| 4,932,975 | A  | * | 6/1990 | Main et al. | 623/17.12 |
|---|---|---|---|---|---|
| 5,146,933 | A | * | 9/1992 | Boyd | 128/899 |
| 5,236,460 | A | * | 8/1993 | Barber | 623/17.15 |
| 6,395,032 | B1 | * | 5/2002 | Gauchet | 623/17.12 |
| 6,533,817 | B1 | * | 3/2003 | Norton et al. | 623/17.16 |
| 7,771,414 | B2 | * | 8/2010 | Trieu | 604/892.1 |
| 7,794,501 | B2 | * | 9/2010 | Edie et al. | 623/17.12 |
| 7,875,075 | B2 | * | 1/2011 | Schwab | 623/17.11 |
| 2003/0135277 | A1 | * | 7/2003 | Bryan et al. | 623/17.12 |
| 2003/0187438 | A1 | * | 10/2003 | Assaker et al. | 606/61 |
| 2004/0024460 | A1 | * | 2/2004 | Ferree | 623/17.12 |
| 2004/0243238 | A1 | * | 12/2004 | Arnin et al. | 623/17.12 |
| 2004/0260396 | A1 | * | 12/2004 | Ferree et al. | 623/17.12 |
| 2005/0055025 | A1 | * | 3/2005 | Zacouto et al. | 606/72 |
| 2005/0060036 | A1 | * | 3/2005 | Schultz et al. | 623/17.15 |
| 2005/0070900 | A1 | * | 3/2005 | Serhan et al. | 606/61 |
| 2006/0064169 | A1 | * | 3/2006 | Ferree | 623/17.12 |
| 2006/0241766 | A1 | * | 10/2006 | Felton et al. | 623/17.12 |
| 2007/0233254 | A1 | * | 10/2007 | Grotz et al. | 623/17.11 |
| 2008/0161933 | A1 | * | 7/2008 | Grotz et al. | 623/17.16 |

* cited by examiner

*Primary Examiner* — Ellen C Hammond
*Assistant Examiner* — Stuart S Bray

(57) ABSTRACT

An intervertebral spacer for positioning between vertebral members. The spacer may include contact surfaces that are configured to contact against the vertebral members. A fluid cylinder may be positioned between the first and second contact surfaces and configured to contain a fluid. The fluid cylinder may include an outer cylinder with an open first end that telescopingly receives an inner cylinder. The spacer is configured to maintain the distance between the contact surfaces at a desired amount.

17 Claims, 7 Drawing Sheets

EXPANDABLE INTERVERTEBRAL SPACERS AND METHODS OF USE

RELATED APPLICATIONS

This application is a continuation of co-pending application Ser. No. 12/848,499, filed on Aug. 2, 2010, which itself is a continuation of application Ser. No. 11/412,671, filed on Apr. 27, 2006, now U.S. Pat. No. 7,794,501. Each of these applications is herein incorporated by reference in its entirety.

BACKGROUND

The present application is directed to devices and methods for stabilizing vertebral members, and more particularly, to intervertebral implants and methods of use for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to an intervertebral spacer for positioning between first and second vertebral members. One spacer includes a first contact surface and a second contact surface. A fluid chamber is positioned between the first and second contact surfaces and is configured to contain a fluid. The fluid chamber includes an outer member with an open end, a sidewall, and a closed end. The outer member telescopingly receives an inner member. A slot is positioned in the sidewall of the outer member and extends inward from the open end. A seal is positioned in the slot to prevent the fluid from leaking from the fluid chamber.

Another spacer includes first and second contact surfaces. A fluid chamber is positioned between the first and second contact surfaces and is configured to contain a fluid. The fluid chamber includes an outer member with an open end that telescopingly receives an inner member. A slot extends through the outer member and intersects with the fluid chamber. An elongated retaining mechanism extends across the slot and includes longitudinal first and second sections with the first section of the retaining mechanism positioned in the outer member on a first side of the slot and the second section of the retaining mechanism positioned in the outer member on an opposing second side of the slot. The outer member is movable relative to the outer member to adjust a width of the slot.

Another spacer includes first and second contact surfaces. A fluid chamber is positioned between the first and second contact surfaces and is configured to contain a fluid. The fluid chamber includes an outer member with an open first end that telescopingly receives an inner member. A slot extends through the outer member at the open first end and intersects with the fluid chamber. A seal is positioned in the slot to prevent the fluid from leaking from the fluid chamber.

DETAILED DESCRIPTION

Figure 1:
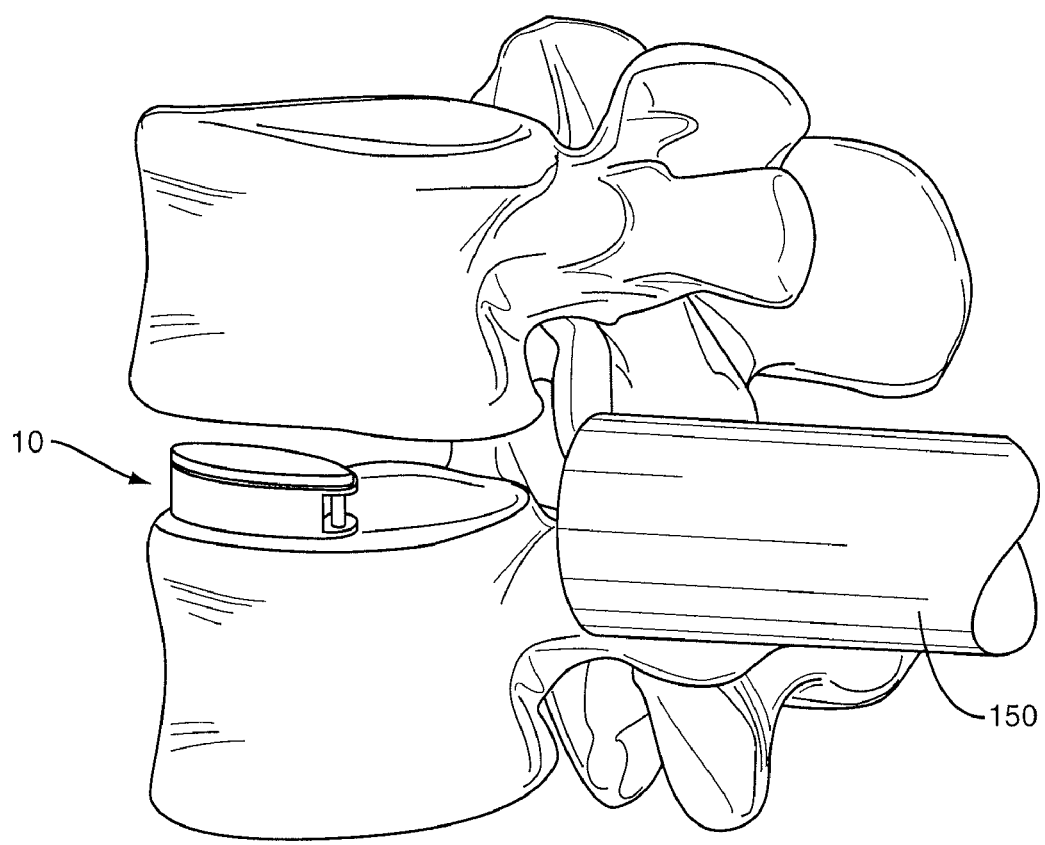
FIG. 1 is a perspective view of an exemplary intervertebral spacer in a retracted position disposed between two vertebral members.
Figure 2:
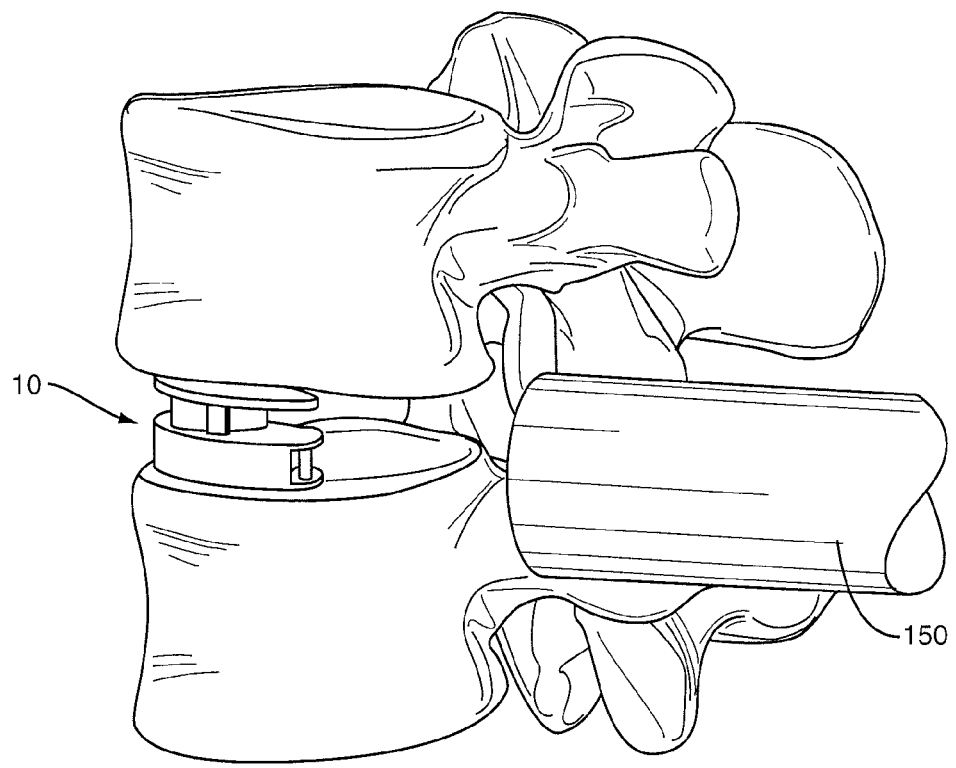
FIG. 2 is a perspective view of an exemplary intervertebral spacer in an extended position disposed between two vertebral members.

The present application relates to implants for replacing an intervertebral disc, vertebral member, or combination of both, and to methods of inserting the same. The implant comprises an intervertebral spacer 10 that can be inserted between vertebral bodies in a compact configuration as shown in FIG. 1 and subsequently expanded to contact the adjacent vertebral bodies as shown in FIG. 2.

Figure 3:
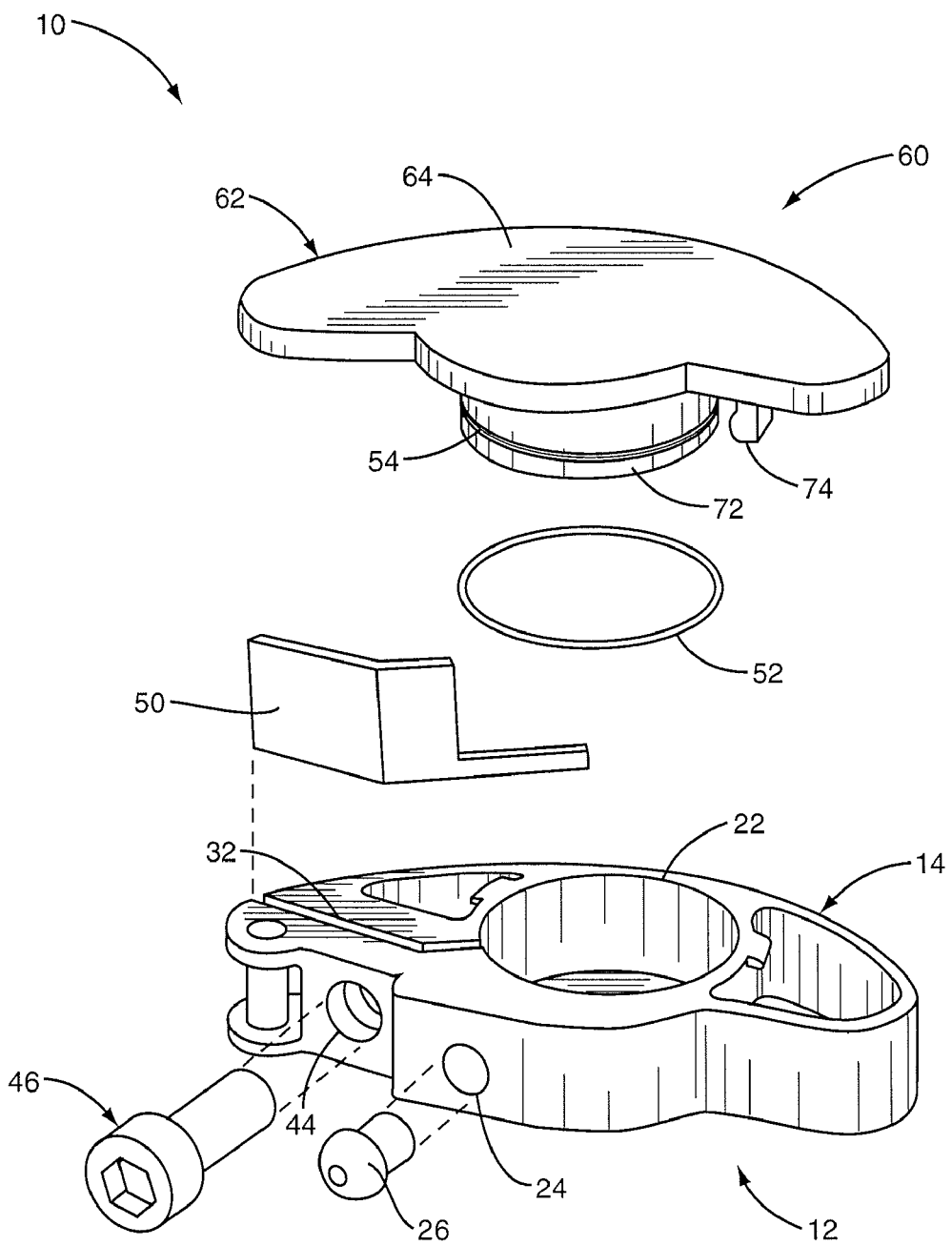
FIG. 3 is an exploded perspective view of an exemplary intervertebral spacer.
Figure 4:
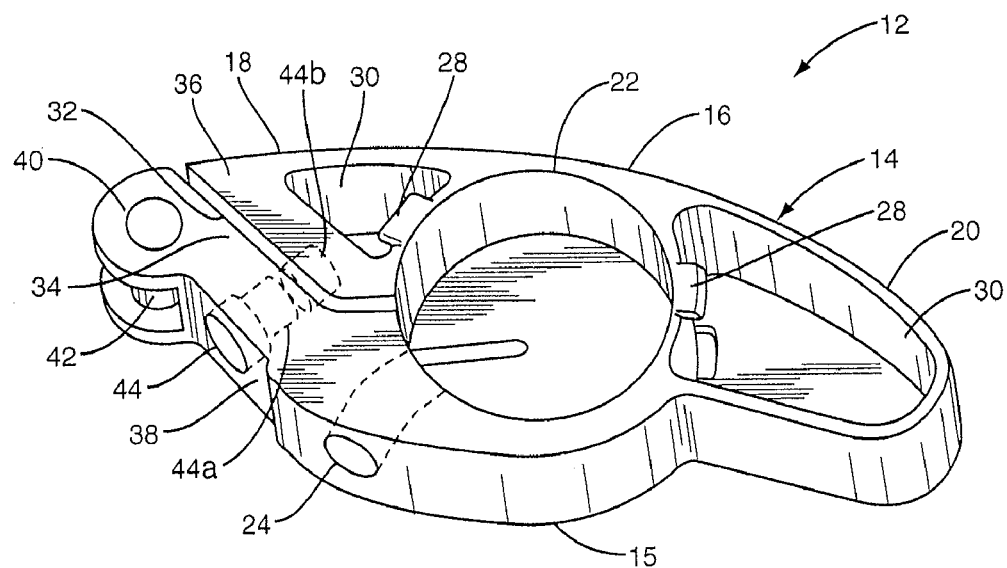
FIG. 4 is a perspective view of an inferior member for an exemplary intervertebral spacer.
Figure 5:
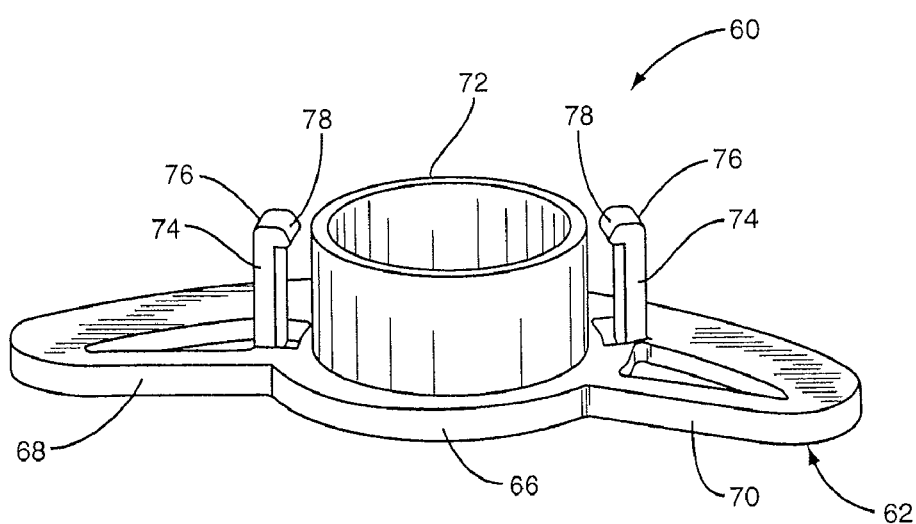
FIG. 5 is a perspective view of a superior member for an exemplary intervertebral spacer.

FIGS. 3-5 illustrate one exemplary embodiment of the intervertebral spacer 10. The intervertebral spacer 10 comprises an inferior member 12 and a superior member 60 movable with respect to the inferior member 12 from a retracted position to an extended position. As will be described in more detail below, the inferior member 12 includes a first cylinder 22, and the superior member 60 includes a second cylinder 72 that is insertable into the first cylinder 22. The cylinders 22 and 72 together define a expansion chamber. When fluid is introduced into the expansion chamber, the superior member 60 is urged away from the inferior member 12. While cylinders 22 and 72 are shown having a circular cross-section, those skilled in the art will appreciate that the cylinders 22 and 72 can have other shapes, such as square, rectangular, oval, kidney-shape, etc.

FIG. 4 illustrates details of one embodiment of the inferior member 12. The inferior member 12 comprises a body 14 including a bottom surface 15 that contacts an adjacent vertebral body. The bottom surface 15 can be textured to grip the vertebral body. For example, teeth, ridges, or grooves can be formed in the bottom surface 15 to improve gripping capability. The body 14 has an oblong configuration including a central section 16 and wing sections 18 and 20. Cylinder 22 is formed in the central section 16. A fluid port 24 is formed in the central section 16 for introducing fluid into the expansion chamber formed by cylinders 22 and 72. A one-way valve 26

(FIG. 3) is disposed in the fluid port 24 that allows introduction of fluid, such as a saline solution, into the expansion chamber, and prevents fluid from exiting the expansion chamber. One or more cavities 30 may be formed in the wing sections 18 and 20 to reduce weight and material requirements.

A slot 32 is formed in the wing section 18. Slot 32 divides the wing section 18 into first and second clamping portions 34 and 36, respectively, and intersects both the wall and bottom of the cylinder 22. A compressible seal 50 is disposed within the slot 32 to prevent fluid from leaking from the expansion chamber. Clamping portion 34 includes a recessed surface 38. A pair of spaced-apart ears 40 project outward from the recessed surface 38 for mounting a pin 42. The ends of the pin 42 are firmly secured in openings formed in the ears 40. Any suitable techniques for securing the pin 42 can be used. A screw hole 44 extends inward from the recessed surface 38 to receive a locking screw 46. The screw hole 44 crosses the slot 32 such that the screw hole 44 is divided into two portions 44a, 44b. Portion 44b of the screw hole 44 is threaded. When the locking screw 46 is tightened, the clamping portions 34 and 36 are pulled together, causing a slight contraction of the cylinder 22. As will be hereinafter described, this clamping arrangement functions as a locking mechanism to lock the superior member 60 firmly in place once proper height adjustment has been made.

The superior member 60, shown in FIG. 5, comprises a plate 62 having a top surface 64 that engages an adjacent vertebral body. The top surface 64 can be textured to grip the vertebral body. For example, small teeth, ridges, or grooves can be formed in the top surface 64 to improve gripping capability. The top plate 62 is shaped to generally correspond to the shape of the inferior member 12. The top plate 62 includes a central section 66 and wing sections 68 and 70. A cylinder 72 extends from the bottom surface of the top plate 62. Cylinder 72 is sized to fit within the cylinder 22 in the inferior member 12. In one embodiment, the interior dimension of the cylinder 22 and exterior diameter of the cylinder 22 are sized to close tolerances such that a seal is formed between the interior wall of cylinder 22 and outer surface of cylinder 72. However, those skilled in the art will appreciate that a ring seal 52 may be used to form a fluid tight seal between cylinders 22 and 72. An annular groove 54 may also be formed in the outer surface of the cylinder 72 to position the seal 52.

A mechanism can be provided to prevent the inferior member 12 and superior member 60 from separating. In one embodiment, a pair of resilient fingers 74 extends downward from the bottom surface of the top plate 62 of superior member 60. The enlarged ends 76 of the resilient fingers 74 are configured to engage the locking tabs 28 on the inferior member 12. When the superior member 60 is assembled with the inferior member 12, the ends of the locking fingers 74 contact the locking tabs 28. Camming surfaces 78 on the enlarged ends 76 of the locking fingers 74 cause the resilient fingers 74 to flex outward and pass over the locking tabs 28. Once the enlarged ends 76 have passed over the locking tabs 28, the resilient fingers 74 return to their original position, thereby preventing separation of the superior member 60. Thus, the resilient fingers 74 and locking tabs 28 cooperate to retain the superior member 60 in place.

Figure 6:
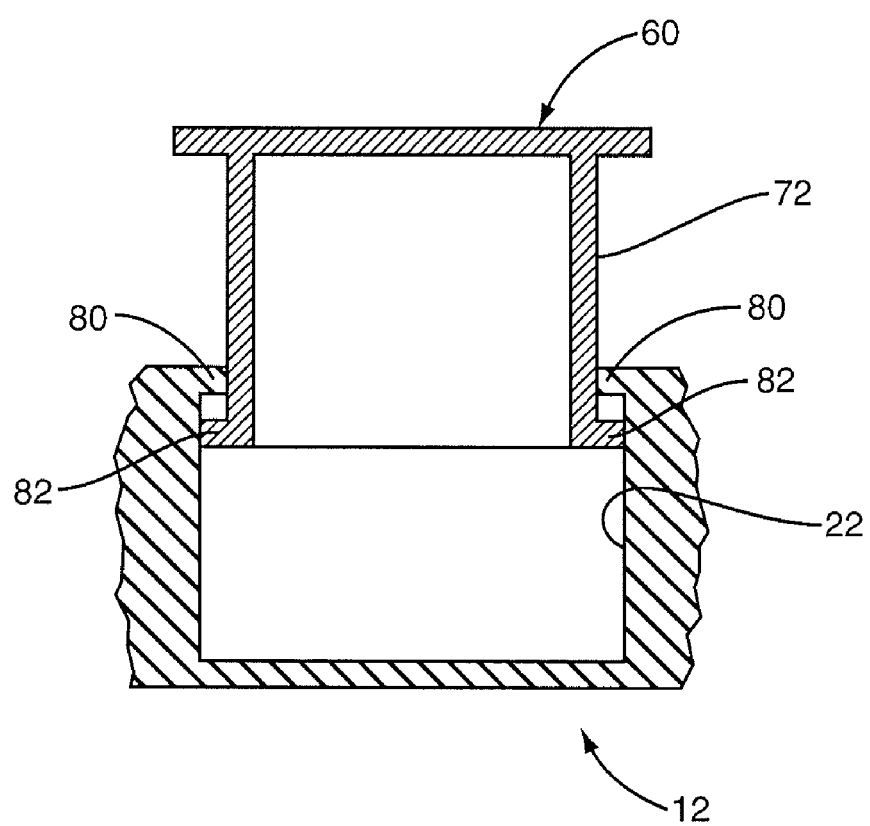
FIG. 6 is a detail view of one exemplary intervertebral spacer.

FIG. 6 illustrates an alternate method of preventing separation of the inferior member 12 and superior member 60. In this embodiment, an inwardly projecting lip 80 is formed at the top end of cylinder 22 and an outwardly projecting lip 82 is formed at the bottom end of cylinder 72. In this embodiment, the superior member 60 can be assembled with the inferior member 12 by dipping the superior member 60 in a cold liquid, such as liquid nitrogen, to shrink the superior member 60. When the superior member 60 shrinks, the lip 82 on cylinder 72 will pass through the lip 80 on cylinder 22. The superior member 60 will then expand to its original size as it returns to ambient temperatures.

The inferior member 12 and superior member 60 can be made of any suitable material, such as PEEK. The bottom of the inferior member 12 and/or top late 62 of the superior member 60 could be porous to allow the in-growth of bone. An embedded biologic coating, such as hydroxia appetite (HA), BMP, or calcium phosphate could be used to promote bone in-growth. The contact surfaces of the inferior and superior members 12 and 72 could also be textured to grip the adjacent vertebral bodies.

In use, the superior member 60 is assembled to the inferior member 12 and placed in a compact configuration with the superior member 60 in a retracted position relative to the inferior member 12 as shown in FIG. 1. The intervertebral spacer 10, in a compact configuration, is inserted through a cannula 150 into an intervertebral space between two vertebral bodies (FIG. 1). Those skilled in the art will appreciate that the intervertebral spacer 10 can replace one or more disks and/or vertebral bodies. After the insertion of the intervertebral spacer 10, fluid or compressed air is introduced into the expansion chamber to cause the superior member 60 to extend away from the inferior member 12 as shown in FIG. 2. The superior member 60 is raised until the contact surfaces of the inferior and superior members 12 and 60 are engaged with the adjacent vertebral bodies. Once the height of the intervertebral spacer 10 is properly adjusted, the locking screw 46 is tightened to lock the superior member 60 in a fixed position relative to the inferior member 12. Tightening the locking screw 46 causes the cylinder 22 of the inferior member 12 to contract and clamp against the exterior surface of cylinder 22. Thus, the cylinder 22 itself functions as a clamp that will lock the inferior and superior members 12, 60 in position, even in the event that fluid leaks from the expansion chamber.

Figure 7:
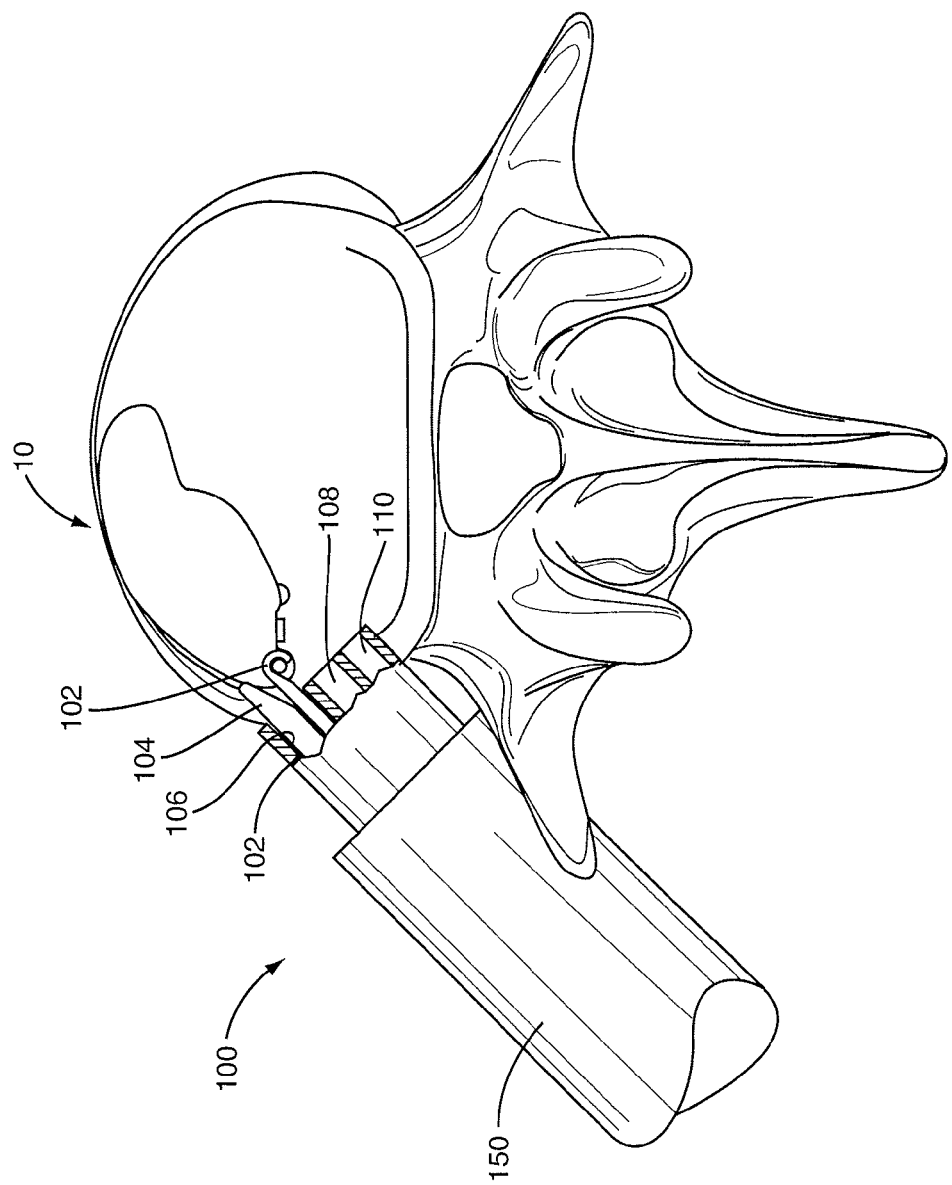
FIGS. 7 and 8 illustrate an exemplary method of inserting the intervertebral spacer.
Figure 8:
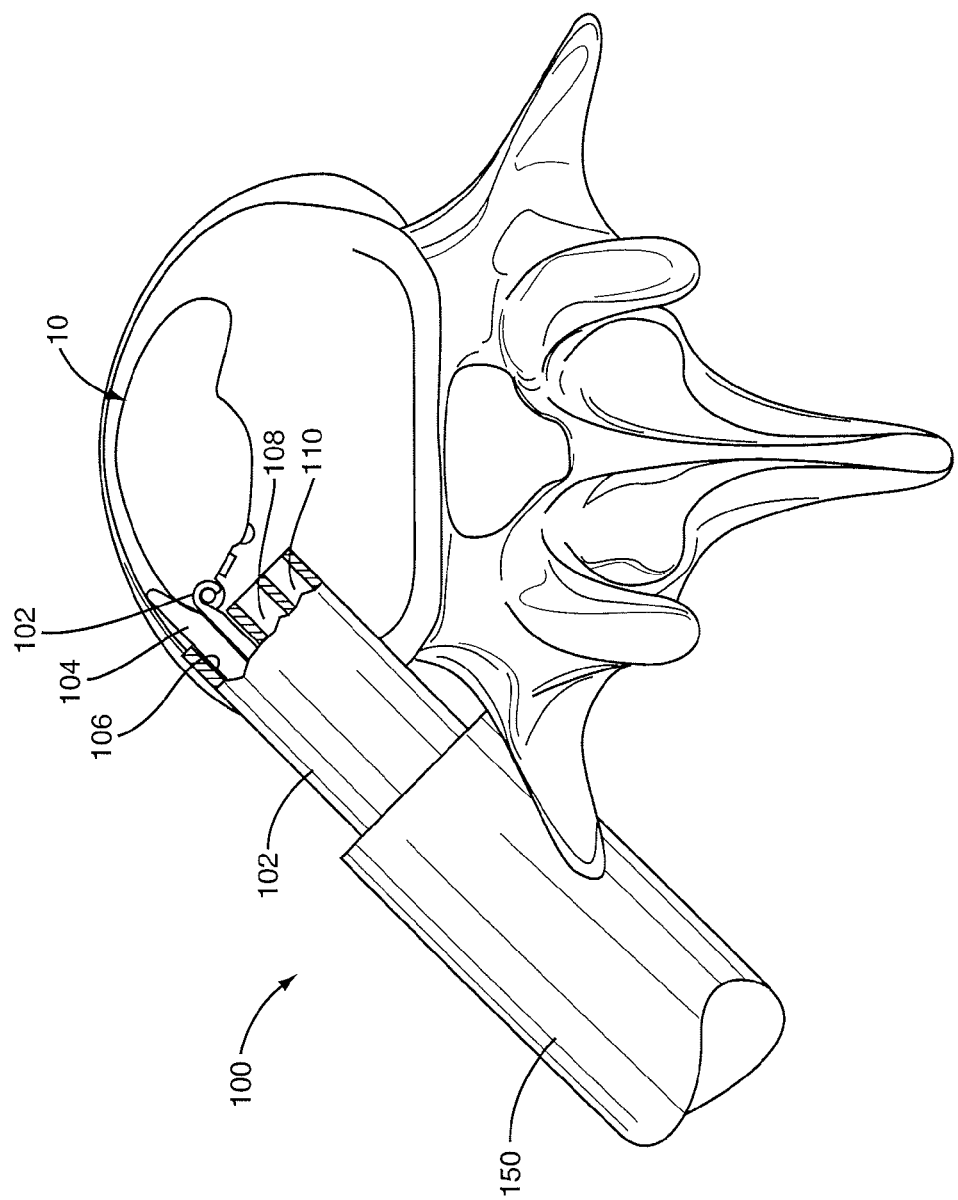

FIGS. 7 and 8 illustrate an exemplary insertion tool 100 to insert the intervertebral spacer 10. The insertion tool 100 includes an elongate housing 102 having three lumens 106, 108, and 110 formed therein. Access to the intervertebral space is gained through a cannula 150 inserted into the body. FIGS. 7 and 8 illustrate the distal end of the cannula 150 and insertion tool 100. The insertion tool 100 includes a hook member 102 that engages pin 42 on the intervertebral spacer 10. As the intervertebral spacer 10 is advanced through the cannula 150, the intervertebral spacer 10 initially assumes the position shown in FIG. 7. When the intervertebral spacer 10 exits from the end of the cannula 150, a push rod 104 is used to rotate the intervertebral spacer 10 into the proper angular position.

The hook member 102 and push rod 104 pass through the first lumen 106. The second lumen 108 aligns with the locking screw 46. The third lumen 110 aligns with the fluid valve 26. After the intervertebral spacer 10 is properly positioned, a fluid delivery line can be inserted through lumen 110 and engaged with the fluid valve 26 to deliver fluid into the expansion chamber to expand the intervertebral spacer 10. A tool can then be inserted through the middle lumen 108 to tighten the locking screw 42.

The embodiments described above include member 60 being a superior member and member 12 being inferior. In another embodiment, the orientation of these members 60, 12 may be interchanged with member 60 functioning as an inferior member and member 12 functioning as a superior member.

One embodiment includes accessing the spine from a postero-lateral approach. Other applications contemplate other approaches, including posterior, anterior, antero-lateral and lateral approaches to the spine, and accessing other regions of the spine, including the cervical, thoracic, lumbar and/or sacral portions of the spine.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An intervertebral spacer comprising:
a first contact surface;
a second contact surface;
a fluid chamber positioned between the first and second contact surfaces and configured to contain a fluid, the fluid chamber including an outer member with an open end, a sidewall, and a closed end, the outer member telescopingly receives an inner member;
a slot in the sidewall of the outer member that extends inward from the open end; and a seal positioned in the slot to prevent the fluid from leaking from the fluid chamber;
a retaining member attached to the outer member with a first section positioned on a first side of the slot and a second section positioned on an opposing second side of the slot; and
wherein the retaining member is rotatably positioned within an opening in the outer member and movable between a first position with a width of the slot being a first distance and a second position with the width of the slot being a smaller second distance.

2. The intervertebral spacer of claim 1, wherein the fluid chamber has a circular cross-sectional shape.

3. The intervertebral spacer of claim 1, further comprising a port that extends through the sidewall of the outer member and includes an inlet, the inlet positioned between the open end and the closed end of the outer member and away from the slot.

4. The intervertebral spacer of claim 1, wherein the outer member is integral with the first contact surface and the inner member is integral with the second contact surface.

5. The intervertebral spacer of claim 1, further comprising a ring seal that extends around an exterior of the inner member and is positioned within the outer member.

6. An intervertebral spacer comprising:
a first contact surface;
a second contact surface;
a fluid chamber positioned between the first and second contact surfaces and configured to contain a fluid, the fluid chamber including an outer member with an open end that telescopingly receives an inner member;
a slot that extends through the outer member and intersects with the fluid chamber; and
an elongated retaining mechanism that extends across the slot and includes longitudinal first and second sections, the first section of the retaining mechanism positioned in the outer member on a first side of the slot and the second section of the retaining mechanism positioned in the outer member on an opposing second side of the slot, the outer member on the first side of the slot being movable relative to the outer member on the opposing second side of the slot to adjust a width of the slot.

7. The intervertebral spacer of claim 6, further comprising a seal positioned in the slot.

8. The intervertebral spacer of claim 7, wherein the seal extends along a sidewall and a closed bottom end of the outer member.

9. The intervertebral spacer of claim 6, wherein the retaining mechanism is a screw with a threaded shaft that engages within threads in an opening of the outer member.

10. The intervertebral spacer of claim 9, wherein the opening of the outer member is spaced away from the fluid chamber.

11. The intervertebral spacer of claim 6, wherein the outer member includes a sidewall that extends between the open end and a closed end, the slot extends inward from the open end along and the sidewall.

12. The intervertebral spacer of claim 6, wherein the outer member is integral with the first contact surface and the inner member is integral with the second contact surface.

13. An intervertebral spacer comprising:
a first contact surface;
a second contact surface;
a fluid chamber positioned between the first and second contact surfaces and configured to contain a fluid, the fluid chamber including an outer member with an open first end that telescopingly receives an inner member;
a slot that extends through the outer member at the open first end and intersects with the fluid chamber;
a seal positioned in the slot to prevent the fluid from leaking from the fluid chamber; and
a screw that extends through an opening in the outer member and across the slot with a first portion of the screw positioned on a first side of the slot and a second portion of the screw positioned on an opposing second side of the slot.

14. The intervertebral spacer of claim 13, wherein the outer member includes a closed second end opposite from the open first end and a sidewall that extends between the ends, the slot extending along the sidewall.

15. The intervertebral spacer of claim 14, wherein the slot further extends along the closed second end.

16. The intervertebral spacer of claim 15, wherein the seal is positioned in the slot and extends along the sidewall and along the closed second end.

17. The intervertebral spacer of claim 14, further comprising a ring seal that extends around an exterior of the inner member and is positioned within the outer member.

* * * * *